United States Patent [19]

Shimizu et al.

[11] 4,021,310

[45] May 3, 1977

[54] METHOD FOR INHIBITING THE POLYMERIZATION OF ACRYLIC ACID OR ITS ESTERS

[75] Inventors: Noboru Shimizu, Takatsuki; Sadao Yoshida, Suita; Kunihiro Kubota, Takatsuki; Takashi Ohara, Nishinomiya, all of Japan

[73] Assignee: Nippon Shokubai Kagaku Kogyo Co., Ltd., Osaka, Japan

[22] Filed: Apr. 18, 1975

[21] Appl. No.: 569,263

Related U.S. Application Data

[63] Continuation of Ser. No. 426,037, Dec. 19, 1973, abandoned.

[52] U.S. Cl. .................................. 203/8; 203/49; 260/526 N
[51] Int. Cl.² ..................... B01D 3/34; C07C 57/04
[58] Field of Search ............... 203/8, 9, 57, 51, 38, 203/49; 260/526 N

[56] References Cited

UNITED STATES PATENTS

| | | | |
|---|---|---|---|
| 2,784,219 | 3/1957 | Couvillon | 203/8 |
| 3,432,401 | 3/1969 | Tcherkuresky | 203/8 |
| 3,433,831 | 3/1969 | Yomiyama et al. | 203/8 |
| 3,462,484 | 8/1969 | Schnizer et al | 203/8 |
| 3,493,471 | 2/1970 | Bashurd | 203/8 |
| 3,527,677 | 9/1970 | Harpring | 203/8 |
| 3,666,794 | 5/1972 | Otsuki et al. | 203/8 X |
| 3,674,651 | 7/1972 | Otsuki et al. | 203/8 |
| 3,794,567 | 2/1974 | Otsuki et al. | 260/526 N |
| 3,816,267 | 6/1974 | Chuang | 203/DIG. 21 |
| 3,888,922 | 6/1975 | Levy et al. | 260/526 N |

*Primary Examiner*—Wilbur L. Bascomb, Jr.
*Attorney, Agent, or Firm*—Sherman & Shalloway

[57] ABSTRACT

A method for inhibiting the polymerization of acrylic acid or acrylic esters during the distillation for separating or purifying the acrylic acid obtained by the vapor phase catalytic oxidation of propylene or acrolein, or the acrylic esters derived from said acrylic acid, said method comprising carrying out the distillation operation in the presence of (A) at least one compound selected from the group consisting of hydroquinone, hydroquinonemonomethyl ether, cresols, phenols, t-butyl catechol, diphenylamine, phenothiazines and methylene blue (B) at least one compound selected from the group consisting of copper dimethyldithiocarbamate, copper diethyldithiocarbamate copper dibutyldithiocarbamate and copper salicylate: and (C) molecular oxygen.

2 Claims, No Drawings

METHOD FOR INHIBITING THE POLYMERIZATION OF ACRYLIC ACID OR ITS ESTERS

This is a continuation of application Ser. No. 426,037, filed Dec. 19, 1973, and now abandoned.

This invention relates to a method for inhibiting the polymerization of acrylic acid or its esters and, in particular, to a method for inhibiting the polymerization of acrylic acid obtained by the vapor-phase catalytic oxidation of propylene or acrolein, or esters derived from said acrylic acid. More specifically, the present invention relates to a method for inhibiting the polymerization of aforesaid acrylic acid or its esters in the distillation operation.

In the process of preparing acrylic acid from propylene or acrolein by the vapor phase catalytic oxidation reaction or in the process of preparing acrylic esters from the so obtained acrylic acid by either the esterification reaction or the transesterification reaction, there is usually used a distillation operation for separating, concentrating or purifying. And it is well known that these acrylic acid and its esters have high polymerization tendency which becomes extremely high at elevated temperatures such as in the distillation step. Hence, in the case of the preparation on a commercial scale of acrylic acid or esters thereof, the prevention of trouble by the polymerization of these compounds during the distillation step is exceedingly important for the stable operation of the process. Especially, in the distillation step being handled under elevated temperatures, it is indispensable to establish an effective technique for preventing the polymerization to conduct the continuous and stable operation.

When distilling acrylic acid or its esters in the separation, concentration or purification step, it is well known that a polymer may be formed at such following places, i.e. the reverse side of the trays, the inside of the bubble caps, the external surface of the downcomers and the recessed portions on the column wall which are not perpetually wetted with a liquid containing polymerization inhibitors, and then the hardware(bolts, nuts, etc.), the packing and the gaskets for setting up the trays at which liquid tends to stagnate. The polymers thus formed do not readily dissolve in acrylic acid, acrylic esters, water or other organic solvents. Further, when the polymer once forms inside the column, it becomes a nucleus of polymerization to cause a gradual accumulation of polymer to finally block the inside of the column and render impossible the continuous distillation operation. Moreover, great difficulty is involved in removing this accumulated polymer.

Hitherto, as a measure to inhibit the polymerization of acrylic acid or esters thereof during their distillation, there was proposed in the specification of the German Laid-Open Pat. No. 2,027,655 a distillation column of a construction in which the reverse side of the trays and the inside wall of the column have been made readily wettable. Aside from this proposal, the method most widely used heretofore for inhibiting the polymerization of these compounds is that of adding a polymerization inhibitor to the distillation column. And as typical polymerization inhibitors, known are phenolic compounds, amine compounds, nitro compounds, quinone compounds and the inorganic salts. These polymerization inhibitors are used either singly or as combinations of two or more thereof or in combination with molecular oxygen. As illustrations of the methods of using these polymerization inhibitors, mention can be made of the method of U.S. Pat. No. 3,666,795 which uses the combination of hydroquinone-phenoloxygen and the method of U.S. Pat. No. 3,674,651 which uses combination of diphenylamine-benzoquinone (or hydroquinonemonomethyl ether)-oxygen.

However, contrary to expectations, these measures that have been proposed for inhibiting the polymerization of acrylic acid or its esters have demonstrated hardly any effects in the case of acrylic acid obtained by the vapor phase catalytic oxidation of propylene or acrolein or esters thereof and cannot be employed in the commercial practice. As a reason for the ineffectiveness of the above-mentioned inhibitors to acrylic acid obtained by the vapor phase catalytic oxidation of propylene or acrolein, or its esters, as compared with acrylic acid prepared by the conventional methods such as by the hydrolysis of acrylonitrile, or its esters, it is presumed that there is contained in the former case as impurities a trace amount of a by-product that act as a polymerization initiator, with the consequence that the compounds possess great polymerizability thereby overcoming the effects obtained by the improvement of the construction of the distillation column or the effects obtained by the addition of polymerization inhibitors such as described above. In the case of the conventional method in which the polymerization inhibitors are added, there are other reasons why this method cannot be employed commercially. One of the reasons is that difficulty is experienced in carrying out the distillation operation because of the use of a relatively large amount of molecular oxygen. Another reason is that since compounds of relatively high volatility are used in a considerably large amount, they become mixed in the distilled acrylic acid or the esters thereof to cause a decline in the quality of the products.

An object of the present invention is to find a method which can inhibit polymerization during the distillation for separating or purifying acrylic acid obtained by the vapor phase catalytic oxidation of propylene or acrolein, or its esters, and thereby to provide a method by which these compounds can be distilled without any trouble.

Other objects and advantages of the present invention will become apparent from the following description.

According to the present invention, there is provided a new method which comprises carrying out the distillation for separating or purifying the acrylic acid obtained by the vapor phase catalytic oxidation of propylene or acrolein or acrylic esters derived from the aforesaid acrylic acid, in the presence of A. at least one compound selected from the group consisting of hydroquinone, hydroquinonemonomethyl ether, cresels, phenols, t-butyl catechol, diphenylamine, phenothiazines (compounds of the formula

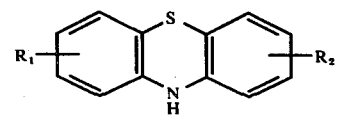

wherein $R_1$ and $R_2$ are each hydrogen or an alkyl group of 1 – 10 carbon atoms), and methylene blue;

B. at least one compound selected from the group consisting of copper dimethyldithiocarbamate, copper diethyldithiocarbamate, copper dibutyldithiocarbamate and copper salicylate; and C. molecular oxygen.

As apparent from what has been previously described, some of the compounds of groups (A) and (B), above, are known as polymerization inhibitors of acrylic acid or its esters. And the simultaneous use of these compounds with molecular oxygen is also known. In contrast to these known methods, the characteristic feature of this invention comprises the simultaneous use of the aforesaid three components of groups (A), (B) and (C) in the distillation of the hereinbefore-noted acrylic acid or its esters, and thereby gaining a synergistic effect, a polymerization inhibiting effect which can not be seen in the conventional methods. The foregoing acrylic esters include in addition to methyl, ethyl, propyl, butyl and 2-ethylhexyl esters of acrylic acid, glycidyl ester and hydroxyalkyl ester having exceedingly high polymerizability.

The invention method is effectively applied in carrying out the preparation of acrylic acid by the vapor phase catalytic oxidation of propylene or acrolein or the preparation of esters from so obtained acrylic acid by either the esterification or the transesterification reaction, the method being applied specifically to the various distillation steps that are carried out in the distillation column for purifying acrylic acid, for purifying acrylic esters, for separating acrylic acid from the solvent, for separating such light fractions as acetic acid from acrylic acid, for separating acrylic acid from acrylic esters and alcohol, for separating such light fraction as acrolein from the aqueous solution of acrylic acid, for separating such light fraction as alcohols from acrylic esters and for separating alcohols from raffinate (the aqueous solution of alcohol and acrylic ester.)

The invention method can also be applied to the various steps that are carried out in the condensation column for acrylic acid and in the esterification reactor, as well as to the storage tank for acrylic acid or acrylic esters.

The foregoing compounds (A) and (B) dissolve with relative ease in water or organic solvents that are used in the process of preparing acrylic acid or its esters. Hence, they can be introduced into the process by dissolving them in the feed or reflux. The molecular oxygen is introduced from the bottom of the distillation column in the gaseous state.

The amounts in which the compounds (A) and (B) and the molecular oxygen (C) are used vary as a rule depending upon the kinds of the compounds (A) and (B) and the operating conditions. For instance, in a distillation column, 10 – 5000 ppm, and especially 10 – 500 ppm, based on the weight of the vapor rising in the column of the compound (A), 5 – 2000 ppm, and especially 10 – 500 ppm, based on the weight of the vapor rising in the column of the compound (B), and 0.01 – 5%, and especially 0.02 – 2% based on the volume of the vapor rising in the column, of the molecular oxygen (C) are preferably caused to be present therein.

The following examples are given for more specifically illustrating the invention.

EXAMPLES 1 – 8 AND CONTROLS 1 – 5

A distillation column of an inside diameter of 150 millimeters having disposed therein 20 steps of stainless steel sieve trays with a spacing of 200 millimeters between the trays and equipped with an overhead line and a reflux line at its top, a feed line at its middle and a still at its bottom was set up so as to be operated continuously.

The compounds (A) and (B) in Table 1 were introduced into the column and dissolving in the reflux liquid in the amounts shown in Table 1. And oxygen was introduced into the column from the bottom in the amount shown in Table 1.

The distillation operation was carried out in a steady manner by continuously distilling off from the top and withdrawing from the bottom products in an amount equalling the liquid fed.

The polymerization inhibiting effect was judged by the pressure loss of the trays or by overhauling to inspect the inside of the column.

Acrylic acid (containing 5 weight % of acetic acid) obtained by the vapor phase catalytic oxidation of acrolein was used as the feed stock, and the distillation operation was carried out by feeding the liquid in an amount of 15 kg/hr and with a reflux ratio of 30 under the conditions of a column top temperature of 45° C., a bottom temperature of 70° C., a column top pressure of 40 mm Hg and a column bottom pressure of 60 mm Hg.

The results obtained are shown in Table 1.

For brevity, the polymerization inhibitors are abbreviated hereinafter as follows:

| | |
|---|---|
| Hydroquinone | HQ |
| Hydroquinonemonomethyl ether | MEHQ |
| Benzoquinone | BQ |
| Cresol | CR |
| Phenol | PH |
| T-butyl catechol | TBC |
| Diphenylamine | DPA |
| Phenothiazine | PTZ |
| Methylene blue | MB |
| Copper dimethyldithiocarbamate | MTC |
| Copper diethyldithiocarbamate | ETC |
| Copper dibutyldithiocarbamate | BTC |
| Copper salicylate | SA |

Table 1

| | Compound (A) ppm by wt. | | Compound (B) ppm by wt. | | Oxygen (C) % by vol. | Results |
|---|---|---|---|---|---|---|
| Example | | | | | | |
| 1 | HQ | 300 | MTC | 15 | 0.15 | No polymer noted when distillation column was overhauled after 3 months |
| 2 | MEHQ | 300 | BTC | 50 | 0.1 | " |
| 3 | PH | 300 | SA | 80 | 0.2 | " |
| 4 | TBC | 300 | BTC | 50 | 0.1 | " |
| 5 | HQ | 200 | BTC | 40 | 0.1 | " |
| | | | MTC | 10 | | |
| 6 | CR | 400 | BTC | 50 | 0.1 | " |
| 7 | DPA | 300 | ETC | 40 | 0.1 | " |
| 8 | MB | 300 | BTC | 30 | 0.1 | " |
| Control | | | | | | |

Table 1-continued

|   | Compound (A) | ppm by wt. | Compound (B) | ppm by wt. | Oxygen (C) % by vol. | Results |
|---|---|---|---|---|---|---|
| 1 | HQ | 1,000 | not added | | 0.2 | After 20 hours, flooding due to polymer occurred |
| 2 | HQ PH | 500 500 | not added | | 0.5 | After 2 days, flooding due to polymer occurred |
| 3 | HQ BQ | 500 100 | not added | | 0.2 | After 4 days, operation became impossible due to increasing of pressure loss |
| 4 | DPA BQ | 500 500 | not added | | 0.2 | After 6 days, operation became impossible due to increasing of pressure loss |
| 5 | not added | | BTC | 300 | 0.2 | Accumulation of polymer noted at the flange and nozzle portions of the column bottom when column was overhauled after 5 days |

As shown in Table 1, in consequence of having used 1000 ppm of HQ and 0.2% of oxygen in Control 1, flooding occurred after 20 hours of operation, and in the case of Control 5, as a result of having used 300 ppm of BTC and 0.2% of oxygen, an accumulation of polymer was noted after 5 days. When the foregoing results are added, i.e., if 1000 ppm of HQ as the compound (A) and 300 ppm of BTC as the compound (B) are used along with 0.4% of oxygen, it is inferable that troubles of some sort or other would appear after 5 days and 20 hours.

In contrast, in the case of Example 5 which was carried out in accordance with the invention method, as a result of having used 200 ppm of HQ as the compound (A), 40 ppm of BTC and 10 ppm of MTC as the compound (B) and 0.1% of oxygen, excellent results were obtained in that no formation of polymer was noted even after the passage of 3 months, despite the fact that the amounts used of the several components were exceedingly small. This fact serves to prove the existence of a synergistic effect as a result of the use in the method of the present invention of the three components of the compound (A), compound (B) and oxygen (C).

EXAMPLES 9 – 11 AND CONTROLS 6 – 9

When the experiments were carried out by using the same apparatus as that used in Example 1 but varying the composition of liquid fed and also the kinds and amounts of the compounds (A) and (B) as well as the amount used of oxygen (C) the results shown in Table 2 were obtained.

Table 2

| Experiment No. | Composition of liquid fed (wt %) | | (A), (B) and (C) | | | Distillation conditions | Column top | Column bottom | Results |
|---|---|---|---|---|---|---|---|---|---|
| Example 9 | acrylic acid acetic acid ethyl acetate | 32.3 3.3 64.4 | (A): HQ (B): MTC (C): O$_2$ | 200 ppm 10 ppm 0.2 vol% | Pressure mmHg Temp. °C Reflux ratio | 140 36 | 160 93 2 | No pressure loss even after 2 months and steady operation possible. |
| Control 6 | Same as that of Example 9 | | (A): HQ (B): not added (C): O$_2$ | 500 ppm 0.2 vol% | Same as those of Example 9 | | | | Abrupt rise in pressure loss after 5 days and flooding occurred. Accumulation of polymer noted atop the trays. |
| Example 10 | acrylic acid acrolein water other light boiling components | 29.1 1.0 67.5 | (A): HQ (B): SA (C): O$_2$ | 200 ppm 100 ppm 0.05 vol% | Pressure mmHg Temp. °C Reflux ratio | normal 80 | — 110 0.5 | Practically no polymer noted when column was overhauled after 3 months' operation. |
| Control 7 | Same as that of Example 10 | | (A): HQ (B): not added (C): O$_2$ | 200 ppm 0.05 vol% | Same as those of Example 10 | | | | Rise in pressure loss after 15 days and when column was overhauled, accumulation of polymer atop the trays at the upper part noted. |
| Example 11 | acrylic acid containing heavy fractions such as polymer | | (A): MEHQ (B): ETC (C): O$_2$ | 300 ppm 30 ppm 0.05 vol% | Pressure mmHg Temp. °C Reflux ratio | 50 72 | 65 85 0.5 | No abnormal pressure loss even after 2 months |
| Control 8 | Same as that of Example 11 | | (A): MEHQ (B): not added (C): O$_2$ | 500 ppm 0.05 vol% | Same as those of Example 11 | | | | Rise in pressure loss after 5 days and when column as overhauled, accumulation of polymer atop the trays at the upper part noted. |
| Control 9 | Same as that of Example 11 | | (A): not added (B): BTC (C): O$_2$ | 300 ppm 0.05 vol% | Same as those of Example 11 | | | | Polymer separated out on the flange and nozzle portions at the lower part of the column, and steady operation terminated after 3 days. |

EXAMPLES 12 – 17 AND CONTROLS 10 – 11

The experiments were carried out by using the same apparatus as that used in Example 1 but varying the liquid fed and also the kinds and amounts used of the compounds (A) and (B) as well as the amount of air (C) used, with the results shown in Table 3.

Table 3

| Experiment No. | Composition of liquid fed (wt. %) | | (A), (B) and (C) | | | | Distillation conditions | Column top | Column bottom | Results |
|---|---|---|---|---|---|---|---|---|---|---|
| Example 12 | methyl acrylate | 98 | (A): | HQ | 300 | ppm | Pressure mmHg | nor-mal | — | No abnormal pressure |
| | methanol | 2 | (B): | BTC | 40 | ppm | Temp. °C | 70 | 80 | loss for more than 3 |
| | | | (C): | air | 0.2 | vol% | Reflux ratio | | 25 | months. |
| Control 10 | Same as that of Example 12 | | (A): | HQ | 500 | ppm | Same as those of Example 12 | | | Accumulation of polymer at the several of the trays at the upper part of the column and column top to result in abnormal operation. |
| | | | (B): | not added | | | | | | |
| | | | (C): | air | 0.2 | vol% | | | | |
| Example 13 | ethyl acrylate | 98 | (A): | HQ | 300 | ppm | Pressure mmHg | 400 | 420 | No abnormality of opera- |
| | ethanol | 2 | (B): | SA | 50 | ppm | Temp. °C | 65 | 85 | tion for more than 3 |
| | | | (C): | air | 0.15 | mol% | Reflux ratio | | 25 | months. |
| Example 14 | butyl acrylate | 85 | (A): | HQ | 100 | ppm | Pressure mmHg | 200 | 240 | No abnormality of opera- |
| | butanol | 15 | | PTZ | 200 | ppm | | | | tion for more than 3 |
| | | | (B): | ETC | 50 | ppm | Temp. °C | 60 | 103 | months. |
| | | | (C): | air | 0.12 | vol% | Reflux ratio | | 6 | |
| Example 15 | crude 2-ethylhexyl | | (A): | MEHQ | 100 | ppm | Pressure mmHg | 10 | 20 | No pressure loss for more than |
| | acrylate containing | | (B): | BTC | 50 | ppm | Temp. °C | 92 | 120 | 2 months, and viscosity |
| | heavy fractions | | (C): | air | 0.1 | vol% | Reflux ratio | | 0.5 | of bottoms liquid was not |
| | such as polymer | | | | | | | | | more than 10 C.P. |
| Control 11 | Same as that of Example 15 | | (A): | MEHQ | 500 | ppm | Same as those of Example 15 | | | After 5 days the viscosity of the bottoms liquid rose, and abnormality of operation occurred. |
| | | | (B): | not added | | | | | | |
| | | | (C): | air | 0.1 | vol% | | | | |
| Example 16 | acrylic acid | 7 | (A): | M3 | 300 | ppm | Pressure mmHg | nor-mal | — | No abnormal pressure |
| | methyl acrylate | 48 | (B): | ETC | 20 | ppm | Temp. °C | 64 | 108 | loss for more than |
| | methanol | 35 | (C): | air | 0.2 | vol% | Reflux ratio | | 2 | 3 months. |
| | water | 10 | | | | | | | | |
| Example 17 | methyl acrylate | 6 | (A): | HQ | 200 | ppm | Pressure mmHg | nor-mal | — | No abnormality of |
| | methanol | 11 | (B): | BTC | 20 | ppm | Temp. °C | 64 | 104 | operation for more |
| | water | 83 | (C): | air | 0.15 | vol% | Reflux ratio | | 5 | than 3 months. |

What is claimed is:

1. A method for inhibiting the polymerization of a member selected from the group consisting of acrylic acid and acrylic acid esters during a distillation process for separating the acrylic acid or the acrylic acid esters derived from said acrylic acid obtained by the vapor phase catalytic oxidation of a member selected from the group consisting of propylene, acrolein, and the acrylic esters derived from said acrylic acid, said method comprising distilling one of said members selected from the group consisting of acrylic acid and acrylic esters in the presence of (A) 10 – 5000 ppm, based on the weight of the vapor rising in the distillation zone, of at least one compound selected from the group consisting of hydroquinone, hydroquinonemonomethyl ether, cresol, phenol, t-butyl catechol, diphenylamine, phenothiazines and methylene blue; (B) 5 – 2000 ppm, based on the weight of the vapor rising in the distillation zone, of at least one compound selected from the group consisting of copper dimethyldithiocarbamate, copper diethyldithiocarbamate, copper dibutyldithiocarbamate and copper salicylate; and (C) 0.01 – 5%, based on the volume of the vapor rising in the distillation zone, of molecular oxygen and then recovering the purified acrylic acid or acrylic esters.

2. The method of claim 1 comprising having (A) in the amount of 10 – 500 ppm, based on the weight of the vapor rising in the distillation zone, of at least one compound selected from the group consisting of hydroquinone, hydroquinonemonomethyl ether, cresol, phenol, t-butyl catechol, diphenylamine, phenothiazines and methylene blue; (B) 10 – 500 ppm 5 – 200 ppm, based on the weight of the vapor rising in the distillation zone, of at least one compound selected from the group consisting of copper dimethyldithiocarbamate, copper diethyldithiocarbamate, copper dibutyldithiocarbamate and copper salicylate; and (C) 0.02 – 2%, based on the volume of the vapor rising in the distillation zone, of molecular oxygen.

* * * * *

UNITED STATES PATENT OFFICE
CERTIFICATE OF CORRECTION

Patent No. 4,021,310          Dated May 3, 1977

Inventor(s) Noboru Shimizu et al.

It is certified that error appears in the above-identified patent and that said Letters Patent are hereby corrected as shown below:

Item 30, please insert the following Foreign Application Priority Data:

-- Dec. 22, 1972  Japan .................... 128184/72 --

Signed and Sealed this thirtieth Day of August 1977

[SEAL]

Attest:

RUTH C. MASON
Attesting Officer

C. MARSHALL DANN
Commissioner of Patents and Trademarks